(12) United States Patent
Fallik

(10) Patent No.: US 6,416,532 B1
(45) Date of Patent: Jul. 9, 2002

(54) BRAIN COOLING APPARATUS AND METHOD

(76) Inventor: Joel Fallik, 56 Arthur Pl., Yonkers, NY (US) 10701

( * ) Notice: Subject to any disclaimer, the term of this patent is extended or adjusted under 35 U.S.C. 154(b) by 0 days.

(21) Appl. No.: 09/405,542

(22) Filed: Sep. 24, 1999

(51) Int. Cl.[7] .................................................. A61F 7/00
(52) U.S. Cl. ........................ 607/109; 607/104; 607/108
(58) Field of Search ................................. 607/104, 108, 607/109, 96

(56) References Cited

U.S. PATENT DOCUMENTS

| | | | | | |
|---|---|---|---|---|---|
| 4,920,963 | A | * | 5/1990 | Brader | 128/402 |
| 5,292,347 | A | * | 3/1994 | Pompei | 607/104 |
| 5,353,605 | A | * | 10/1994 | Naaman | 62/253.2 |
| 5,545,196 | A | * | 8/1996 | Falk | 607/105 |
| 5,913,885 | A | * | 6/1999 | Klatz et al. | 607/104 |
| 5,916,242 | A | * | 6/1999 | Schwartz | 607/113 |

* cited by examiner

*Primary Examiner*—Linda C. M Dvorak
*Assistant Examiner*—Jocelyn D Ram
(74) *Attorney, Agent, or Firm*—Baker Botts L.L.P.

(57) ABSTRACT

An apparatus for cooling the brain of a patient includes a housing for engagement on a neck of the patient and one or more nozzles for receiving a coolant fluid from an external coolant source and providing a directed mist of the coolant. The nozzles are mounted within the housing and are aligned such that the mist of coolant is directed to the neck of the patient. The apparatus can include a brain temperature sensor operatively coupled to a controller to regulate the discharge of the mist of coolant to maintain a desired brain temperature.

16 Claims, 3 Drawing Sheets

BRAIN COOLING APPARATUS AND METHOD

FIELD OF THE INVENTION

The present invention relates generally to medical apparatus and more particularly relates to a medical apparatus for cooling the brain of patient undergoing a medical procedure

BACKGROUND OF THE INVENTION

It is well known in the medical community that brain cells are susceptible to damage and ultimately death, when subjected to temperature extremes. The body normally is capable of regulating the temperature at a safe level, such as 98.6° Fahrenheit. However, if the body is subjected to an illness which induces extreme fever or if a medical procedure is taking place which elevates the temperature of the blood flowing in the patient, brain damage may result unless measures are taken to ensure that the brain temperature remains below 108° Fahrenheit. For example, if a patient is undergoing microwave therapy, as described in U.S. Pat. No. 5,922,013, a patient's body is subjected to local heating. This local heating may result in excess brain temperature unless the brain temperature is independently controlled from the region undergoing microwave heating.

SUMMARY OF THE INVENTION

It is an object of the present invention to provide an apparatus for cooling the brain of a patient in a rapid and controlled manner.

It is a further object of the present invention to provide a method for cooling the brain of a patient in a rapid and controlled manner.

An apparatus for cooling the brain of a patient includes a housing for engagement on a neck of the patient and one or more nozzles for receiving a coolant fluid from an external coolant source and providing a directed mist of the coolant. The nozzles are mounted within the housing and are aligned such that the mist of coolant is directed to the neck of the patient.

The brain cooling apparatus can include a pump interposed between the nozzles and the external coolant.

The brain cooling apparatus can also include a brain temperature sensor for measuring the temperature of the brain of the patient and a controller which is coupled to the brain temperature sensor and provides a signal to the pump to adjust the coolant discharge rate in response to a measured brain temperature. Generally, the signal from the controller directs the pump to increase the coolant discharge rate when the measured brain temperature exceeds a maximum brain temperature value and directs the pump to decrease the coolant discharge rate when the measured brain temperature is below a minimum brain temperature value.

The housing can also include a fluid discharge port to establish fluid communication with a fluid collection vessel.

A method for cooling the brain of a patient includes the steps of directing a fluid mist discharge onto the neck of a patient, measuring the temperature of the brain, and altering the fluid mist discharge in response to the measured brain temperature to maintain a desired brain temperature. The altering step can increase a discharge rate of the fluid mist if the measured brain temperature exceeds a maximum brain temperature value and decrease the discharge rate of the fluid mist if the measured brain temperature is below a minimum brain temperature value.

BRIEF DESCRIPTION OF THE DRAWINGS

Further objects, features and advantages of the invention will become apparent from the following detailed description taken in conjunction with the accompanying figures showing illustrative embodiments of the invention, in which.

Figure 1:
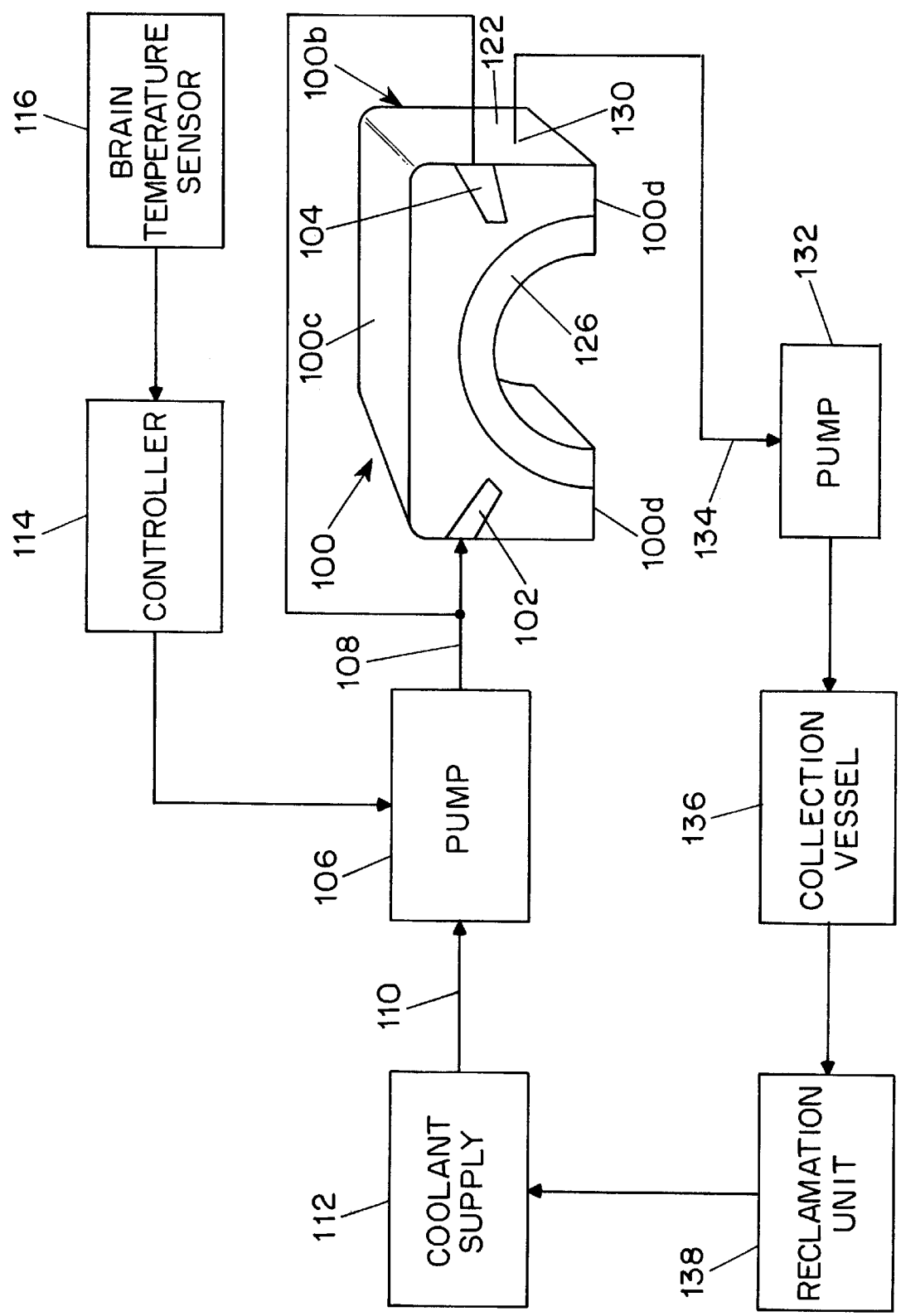
FIG. 1 is a block diagram of an embodiment of the present brain cooling system.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF PREFERRED EMBODIMENTS

Figure 2:
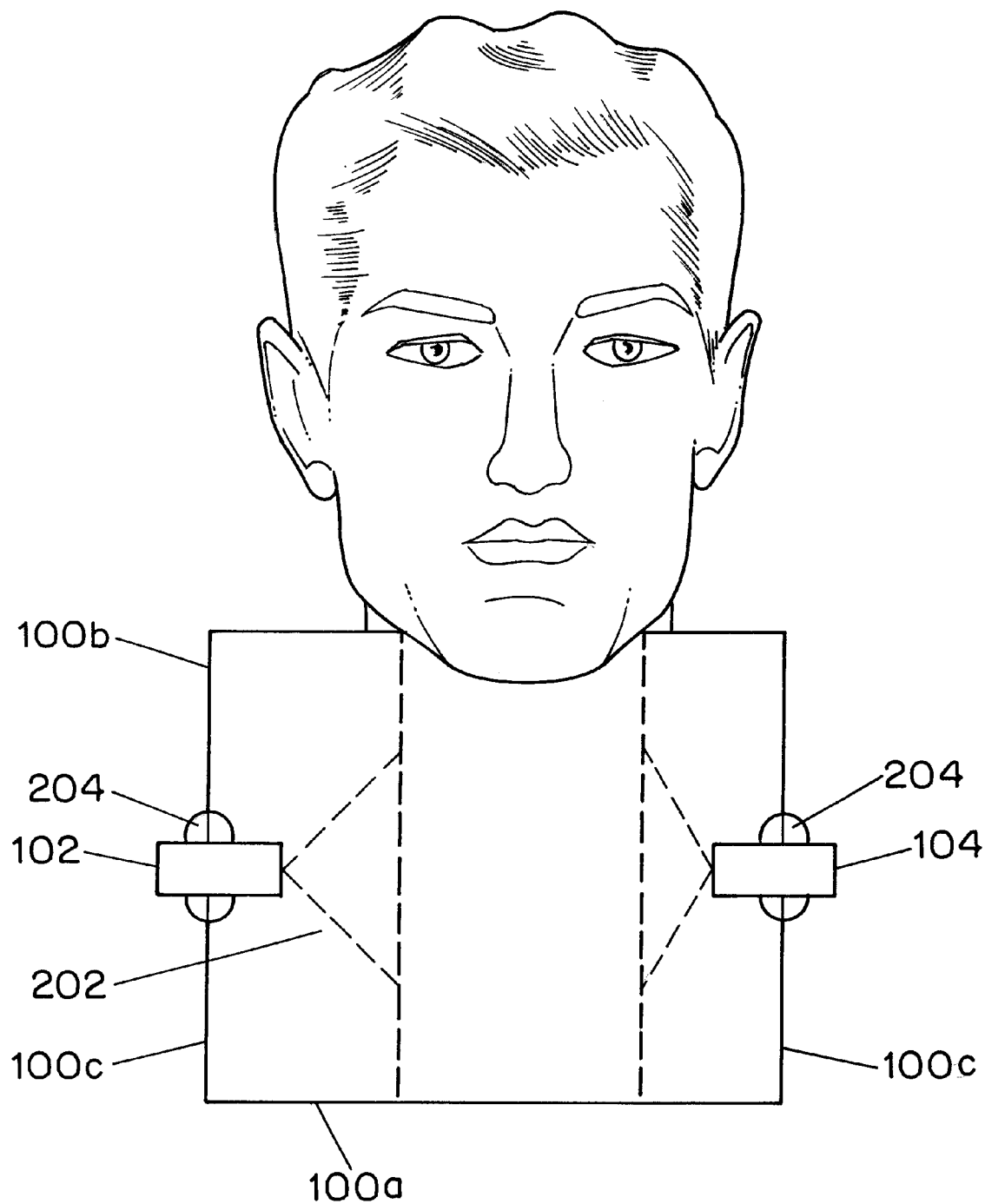
FIG. 2 is a top cross-sectional view of the housing portion of the brain cooling system of FIG. 1, engaged upon the neck of a patient.

In general, the term patient, as used herein, refers to a human being or other animal undergoing treatment with the present apparatus and methods. Referring to FIG. 1 and FIG. 2, the present brain cooling apparatus includes a housing 100 which is adapted to engage the neck of a patient and provide a substantially fluid tight seal therewith. Within the housing 100 are a first cool mist nozzle 102 and a second cool mist nozzle 104. The cool mist nozzles 102, 104 are in fluid communication with a pump 106 through conduit 108. The pump 106 is coupled via fluid conduit 110 to a coolant fluid supply vessel 112. The pump 106 preferably provides a variable flow rate and operates in response to control signals provided by controller 114 which in turn is responsive to a signal from a brain temperature sensor 116. Alternatively, the coolant fluid supply vessel 112 can contain a pressurized coolant and pump 106 can be replaced with an electronically controllable fluid regulator valve.

The coolant provided in coolant supply vessel 112 can be any fluid known to provide significant cooling. This can include refrigerants, such as liquid nitrogen, which rapidly evaporate to effect cooling or fluids which exhibit a very low freezing point and are chilled to an appropriately low temperature by a refrigerator unit within the coolant supply vessel 112 or downstream therefrom. For example, a chilled alcohol solution may provide sufficient cooling.

The brain temperature sensor 116 can take any form known in the art for measuring the temperature of brain tissue. The brain temperature sensor 116 provides a signal indicative of the brain temperature of the patient to the controller 114. In response, the controller 114 processes the brain temperature sensor signal to determine whether the brain is within an acceptable range of temperatures ($T_D \pm \Delta$), which can be predetermined or set by an operator using a suitable interface device (not shown) to the controller 114. The controller 114 provides a signal to the pump 106 to control the fluid flow from the coolant supply vessel 112 through conduits 110 and 108 to the cool mist nozzles 102, 104. If the brain temperature exceeds a desired temperature range ($T_D \pm \Delta$), the controller 114 can direct the pump 106 to increase the fluid flow. Similarly, if the brain temperature is below a desired temperature, the controller 114 can direct the pump 106 to reduce the fluid flow. The desired brain temperature can be any temperature below 108° F., including temperatures which induce safe levels of brain hypothermia.

The housing 100 has a front face 100a and a back face 100b which are separated by a side wall 100c and bottom wall sections 100d to establish a fluid containing chamber when the housing is engaged on the neck of a patient. Both the front face 100a and the back face 100b have substantially semicircular cutaways which are sized and shaped to form a sealing engagement with the neck of a patient. The resulting housing can be described as an inverted U-shaped housing. Compliant diaphragm member 126 can be used along the perimeter of the openings to facilitate a comfortable, yet fluid tight seal with the neck of the patient.

The first cool mist nozzle 102 and second cool mist nozzle 104 are mounted in the housing 100 such that a fine mist from each nozzle is directed onto a region of the neck over the carotid arteries of the patient when the housing is properly engaged on the neck of the patient. The nozzle should provide a minimum practicable droplet size for the selected coolant. It is also desirable that the nozzle provide an elongate spray pattern, such as a fan shaped pattern 202, which substantially extends along the neck region over the carotid arteries. The nozzle attributes contribute to provide a maximum cooling effect as the surface area of the coolant impinging upon the neck of the patient is maximized Preferably, the nozzles 102, 104 are mounted on adjustable brackets 204 such that the angular direction of the nozzle, as well as the distance of the nozzle from the patient's neck, can be adjusted to suit an individual patient.

A fluid discharge port 130 can also be included in the housing 100 to provide a return path for coolant which is discharged from the first cool mist nozzle 102 and second cool mist nozzle 104. The recovered coolant can be in the form of a vapor, a liquid, or both depending on the coolant selected. The state of the recovered coolant will determine the location of the discharge port. In the case where the discharge is heavier than air, the discharge port 130 can be located on a lower portion of the housing 100. In the case where the discharge is lighter than air, the discharge port 130 can be located on an upper portion of the housing 100. The discharge port 130 is preferably in fluid communication with a pump 132 via conduit 134. The pump 132 forces the coolant collected in the housing 100 into a collection vessel 136 via fluid conduit 138. Alternatively, the collection vessel 136 can be placed below the housing 100 and a gravity feed system can be used to transfer fluid from the housing 100 to the collection vessel 136. Preferably, the fluid collection vessel can be further coupled to a coolant reclamation unit 138 which can condense, chill and otherwise restore the coolant to its original state and return the restored coolant fluid to the coolant supply vessel 112. In this way, a closed system is established whereby a majority of the coolant fluid is continuously re-circulated.

By directly impinging the carotid arteries with a fine mist of a coolant fluid, the blood flowing to the brain is rapidly cooled, resulting in cooling of the brain tissue or maintaining the brain tissue at a safe temperature. The rate of cooling is determined by the temperature of the coolant, the rate of evaporation of the coolant and the volume of the coolant being applied to the surface of the neck proximate the carotid arteries. The thermal resistance of the tissue interposed between the surface of the patient's neck and the carotid artery will also effect the cooling rate. The orifice diameter and spray pattern of the nozzles 102, 104 can be selected in cooperation with the flow rate range of the pump 106 and the selected coolant provided in coolant supply 112 to effect an effective cool mist application. The flow of coolant, within the discharge range of the selected pump 106, is controlled by the controller 114 in response to a signal from the brain temperature sensor 116. Thus, a closed loop control system is established whereby the brain temperature is positively regulated despite the aforementioned variables, such as tissue thermal resistance.

Figure 3:
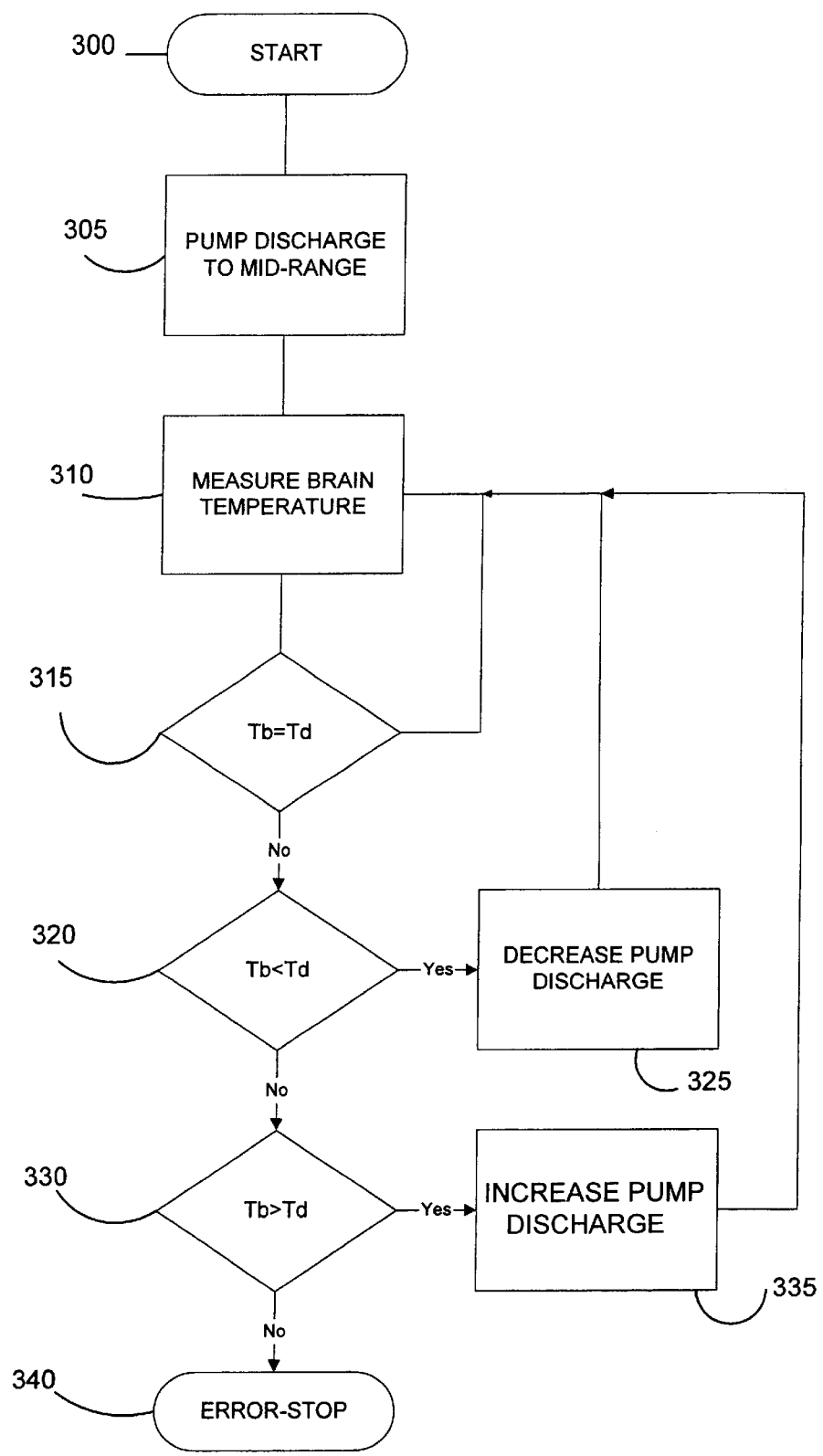
FIG. 3 is a flow chart illustrating a method of cooling a brain in a controlled manner.

FIG. 3 is a flow chart illustrating a method of maintaining the brain of a patient in a desired temperature range ($T_D \pm \Delta$), where $T_D$ is the nominal desired brain temperature and $\Delta$ is a constant which provides a range of hystereses in the control system. After initialization 300, the controller 114 sets the pump 106 to a flow rate approximately in the center of the range of operation of the pump (step 305). A brain temperature measurement is taken to determine the current brain temperature ($T_B$) (step 310). This can be an instantaneous measurement or an average of several samples taken over a known time period.

The measured brain temperature ($T_B$) is then compared against the desired temperature range ($T_D \pm \Delta$)(step 315). If the brain temperature is within the desired range, the coolant flow rate is acceptable and control is returned to step 310 for a new brain temperature measurement. If the brain temperature is below the minimum desired brain temperature value (step 320), the flow of coolant is reduced (step 325) and the process returns to step 310. If the brain temperature is above the maximum desired brain temperature value (step 330), the coolant flow rate is increased (step 335) and the process returns to step 310. If the condition of steps 315, 320 and 330 all fail, this indicates an error and control is terminated (step 340).

The apparatus and methods described herein use direct impingement of a fine mist of coolant to effect a rapid and controlled cooling the brain of a patient. Such rapid and controlled cooling of the brain provides for maintaining the brain at a temperature lower than a portion of a patient's body which is undergoing medical microwave, or other local heating treatment. Such rapid and controlled cooling of the brain can also be used to induce brain hypothermia, and unconsciousness, without medication.

Although the present invention has been described in connection with specific exemplary embodiments, it should be understood that various changes, substitutions and alterations can be made to the disclosed embodiments without departing from the spirit and scope of the invention as set forth in the appended claims.

What is claimed is:

1. An apparatus for cooling the brain of a patient comprising:
    a housing for engagement on a neck of the patient;
    at least one nozzle for receiving a coolant fluid from an external coolant source and providing a directed mist of the coolant, said at least one nozzle being mounted within said housing and aligned such that the mist of the coolant is directed to the neck of the patient;
    a pump interposed between said at least one nozzle and the external coolant source;
    a brain temperature sensor for measuring the temperature of the brain of the patient; and
    a controller, said controller being coupled to said brain temperature sensor and providing a signal to said pump to adjust a coolant discharge rate in response to a measured brain temperature.

2. The apparatus for cooling the brain of a patient of claim 1, wherein the signal from said controller directs the pump to increase the coolant discharge rate when the measured brain temperature exceeds a maximum brain temperature value.

3. The apparatus for cooling the brain of a patient of claim 1, wherein the signal from said controller directs the pump to decrease the coolant discharge rate when the measured brain temperature is below a minimum brain temperature value.

4. The apparatus for cooling the brain of a patient of claim 1, further comprising a fluid collection vessel, and wherein said housing includes a fluid discharge port in fluid communication with said fluid collection vessel.

5. The apparatus for cooling the brain of a patient of claim 1, wherein said at least one nozzle includes two nozzles, with one nozzle directed to each carotid artery of a patient.

6. The apparatus for cooling the brain of a patient of claim 1, wherein said at least one nozzle projects a fan shaped discharge pattern.

7. An apparatus for cooling the brain of a patient comprising:
   a housing for engagement on a neck of the patient;
   at least one nozzle for receiving a coolant fluid from an external coolant source and providing a directed mist of the coolant, said at least one nozzle being mounted within said housing and aligned such that the mist of the coolant is directed to the neck of the patient;
   a pump interposed between said at least one nozzle and the external coolant source;
   a brain temperature sensor for measuring the temperature of the brain of the patient; and
   a controller, said controller being coupled to said brain temperature sensor and providing a signal to said pump to adjust a coolant discharge rate in response to a measured brain temperature,
   wherein said at least one nozzle is mounted on an adjustable bracket such that an angular direction and a distance of said at least one nozzle to the neck of a patient can be altered.

8. A method for cooling the brain of a patient comprising:
   directing a fluid mist discharge onto the neck of a patient;
   measuring the temperature of the brain;
   altering the fluid mist discharge in response to the measured brain temperature to maintain a desired brain temperature.

9. The method for cooling the brain of claim 8, wherein the altering step further comprises increasing a discharge rate of the fluid mist if the measured brain temperature exceeds a maximum brain temperature value and decreasing the discharge rate of the fluid mist if the measured brain temperature is below a minimum brain temperature value.

10. A system for cooling the brain of a patient comprising:
    a coolant fluid supply vessel;
    a pump, said pump being in fluid communication with said fluid supply vessel;
    a housing for engagement on a neck of the patient;
    at least one nozzle, said at least one nozzle in fluid communication with said pump and providing a directed mist of the coolant, said at least one nozzle being mounted within said housing and aligned such that the mist of coolant is directed to the neck of the patient;
    a brain temperature sensor for measuring the temperature of the brain of the patient; and
    a controller, said controller being coupled to said brain temperature sensor and providing a signal to said pump to adjust a coolant discharge rate in response to a measured brain temperature.

11. The system for cooling the brain of a patient of claim 10, wherein the signal from said controller directs the pump to increase the coolant discharge rate when the measured brain temperature exceeds a maximum brain temperature value.

12. The system for cooling the brain of a patient of claim 10, wherein the signal from said controller directs the pump to decrease the coolant discharge rate when the measured brain temperature is below a minimum brain temperature value.

13. The system for cooling the brain of a patient of claim 10, further comprising a fluid collection vessel, and wherein said housing includes a fluid discharge port in fluid communication with said fluid collection vessel.

14. The system for cooling the brain of a patient of claim 10, wherein said at least one nozzle includes two nozzles, with one nozzle directed to each carotid artery of a patient.

15. The system for cooling the brain of a patient of claim 10, wherein said at least one nozzle projects a fan shaped discharge pattern.

16. A system for cooling the brain of a patient comprising:
    a coolant fluid supply vessel;
    a pump, said pump being in fluid communication with said fluid supply vessel;
    a housing for engagement on a neck of the patient;
    at least one nozzle, said at least one nozzle in fluid communication with said pump and providing a directed mist of the coolant, said at least one nozzle being mounted within said housing and aligned such that the mist of coolant is directed to the neck of the patient;
    a brain temperature sensor for measuring the temperature of the brain of the patient; and
    a controller, said controller being coupled to said brain temperature sensor and providing a signal to said pump to adjust the coolant discharge rate in response to a measured brain temperature,
    wherein said at least one nozzle is mounted on an adjustable bracket such that an angular direction and a distance of said at least one nozzle to the neck of a patient can be altered.

* * * * *